(12) United States Patent
Zhang et al.

(10) Patent No.: US 9,079,892 B2
(45) Date of Patent: Jul. 14, 2015

(54) METHOD FOR PREPARING RIVAROXABAN INTERMEDIATE

(71) Applicants: CHINA NATIONAL MEDICINES GUORUI PHARMACEUTICAL CO., LTD., Huianan, Anhui (CN); SHANGHAI INSTITUTE OF PHARMACEUTICAL INDUSTRY, Shanghai (CN)

(72) Inventors: Fuli Zhang, Shanghai (CN); Bin Liang, Shanghai (CN); Chunbo Yang, Shanghai (CN); Chonghao Liu, Shanghai (CN); Yang Gao, Shanghai (CN); Jian Wang, Anhui (CN); Min Jiang, Anhui (CN)

(73) Assignees: CHINA NATIONAL MEDICINES GUORUI PHARMACEUTICAL CO., LTD., Anhui (CN); SHANGHAI INSTITUTE OF PHARMACEUTICAL INDUSTRY, Shanghai (CN)

( * ) Notice: Subject to any disclaimer, the term of this patent is extended or adjusted under 35 U.S.C. 154(b) by 0 days.

(21) Appl. No.: 14/380,875

(22) PCT Filed: Feb. 22, 2013

(86) PCT No.: PCT/CN2013/071769
§ 371 (c)(1),
(2) Date: Aug. 25, 2014

(87) PCT Pub. No.: WO2013/123893
PCT Pub. Date: Aug. 29, 2013

(65) Prior Publication Data
US 2015/0038704 A1    Feb. 5, 2015

(30) Foreign Application Priority Data
Feb. 24, 2012    (CN) .......................... 2012 1 0044359

(51) Int. Cl.
*C07D 413/10*    (2006.01)
*C07D 413/14*    (2006.01)

(52) U.S. Cl.
CPC ............ *C07D 413/10* (2013.01); *C07D 413/14* (2013.01)

(58) Field of Classification Search
CPC ............................ C07D 413/14; C07D 413/10
See application file for complete search history.

(56) References Cited

U.S. PATENT DOCUMENTS

| | | |
|---|---|---|
| 7,816,355 B1 | 10/2010 | Bodhuri et al. |
| 2005/0182055 A1 | 8/2005 | Berwe et al. |
| 2010/0081807 A1 | 4/2010 | Thomas |
| 2011/0034465 A1 | 2/2011 | Bodhuri et al. |
| 2013/0316999 A1 | 11/2013 | STRAUB et al. |

FOREIGN PATENT DOCUMENTS

| | | |
|---|---|---|
| CN | 102250076 A | 11/2011 |
| CN | 103288814 A | 9/2013 |
| DE | 103 00 111 A1 | 7/2004 |
| EP | 1 403 267 A1 | 3/2004 |
| WO | WO 01/47919 A1 | 7/2001 |
| WO | WO 2005/068456 A1 | 7/2005 |
| WO | WO 2011/080341 A1 | 7/2011 |
| WO | WO 2011/098501 A1 | 8/2011 |

OTHER PUBLICATIONS

May 30, 2013 International Search Report issued in International Application No. PCT/CN2013/071769 (with English Translation).
May 30, 2013 Written Opinion issued in International Application No. PCT/CN2013/071769 (with English Translation).

*Primary Examiner* — Rebecca Anderson
(74) *Attorney, Agent, or Firm* — Oliff PLC

(57) ABSTRACT

A method for preparing a Rivaroxaban intermediate I is presented, including the following step: in a non-protonic solvent, under the effect of lewis acid, performing cyclization reaction on 4-(4-phenyl isocyanate)morpholine-3-ketone (II) and (S)-epoxy compound (III), the reaction temperature ranging from 20° C. to 60° C., where R is amino replaced by amino protecting group. The preparation method of the present invention has a mild condition, a simple process, a low cost, and high efficiency; the product is easy to purify and the method is applicable to industrial production.

11 Claims, No Drawings

METHOD FOR PREPARING RIVAROXABAN INTERMEDIATE

CROSS REFERENCE TO RELATED APPLICATION

The present application is the U.S. national stage application of International Application PCT/CN2013/071769, filed Feb. 22, 2013, which international application was published on Aug. 29, 2013, as International Publication WO2013/123893. The International Application claims priority of Chinese Patent Application 201210044359.X, filed Feb. 24, 2012, the contents of which are incorporated herein by reference in their entireties.

FIELD OF INVENTION

The present invention relates to a novel method for preparing pharmaceutical intermediates, particularly relates to a novel method for preparing (S)-(2-oxo-3-(4-(3-oxomorpholino)phenyl)oxazolidin-5-yl)methyl substituted compound, an important intermediate for anticoagulant, Rivaroxaban.

PRIOR ARTS

Rivaroxaban, 5-chloro-N-(((5S)-2-oxo-3-(4-(3-oxomorpholino-4-yl)phenyl)-1,3-oxazolidin-5-yl)methyl) thiophene-2-carboxamide, which has the following structure (V):

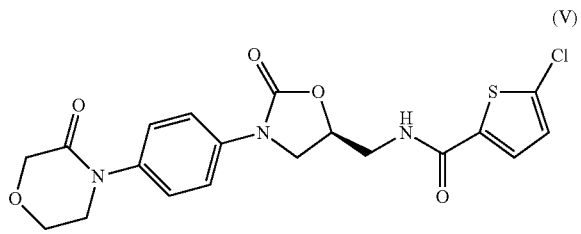 [SMILES: O=C(NC[C@H]1CN(c2ccc(N3CCOCC3=O)cc2)C(=O)O1)c1ccc(Cl)s1]
(V)

Rivaroxaban, developed by Bayer, is an orally active coagulation Factor Xa inhibitor for treating thrombus. It is a direct Factor Xa inhibitor with high selection, and can interrupt the intrinsic and extrinsic pathway of the blood coagulation cascade by inhibiting coagulation Factor Xa, which finally inhibits the formation of thrombin thrombus.

(S)-(2-oxo-3-(4-(3-oxomorpholino)phenyl)oxazolidin-5-yl)methyl substituted compound with the structure (I) is an important intermediate for preparing Rivaroxaban. This intermediate reacts with 5-chlorothiophene-2-formyl chloride to prepare Rivaroxaban after removing the protecting group.

Current synthesis routes for Rivaroxaban are described as follow:

1, WO0147919 disclosed the following synthesis route:

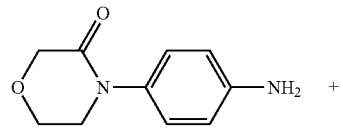
+

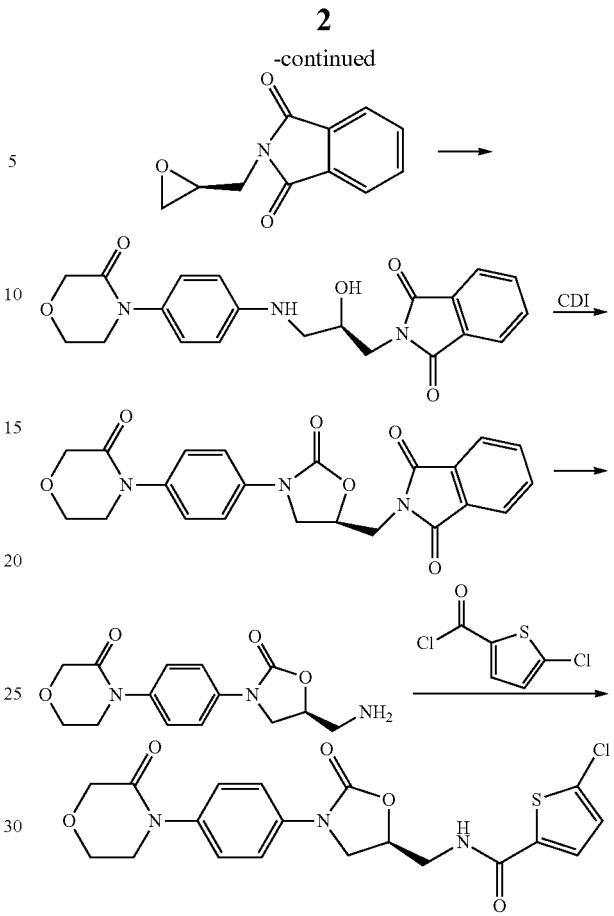

The first step of the route is complicated to operate: (S)-2-(oxiran-2-ylmethyl)isoindoline-1,3-dione is added in batches, and at the same time, the product has to be filtered out constantly, or disubstituted product is easy to be formed which would influence the purity of the product.

2, US20110034465 disclosed the following synthesis route:

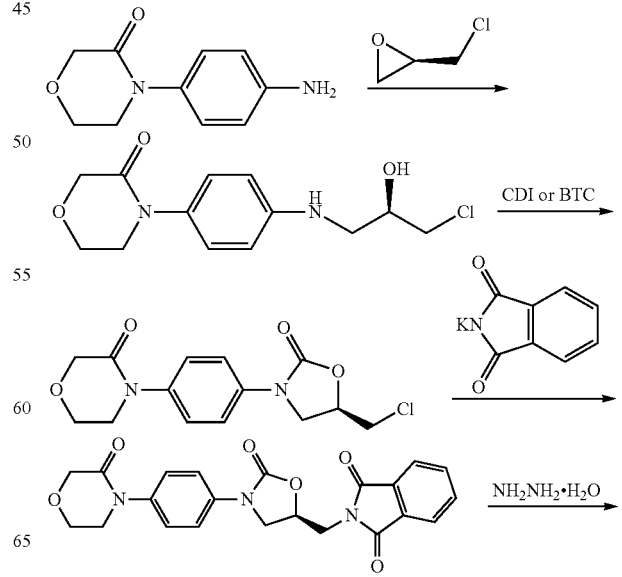

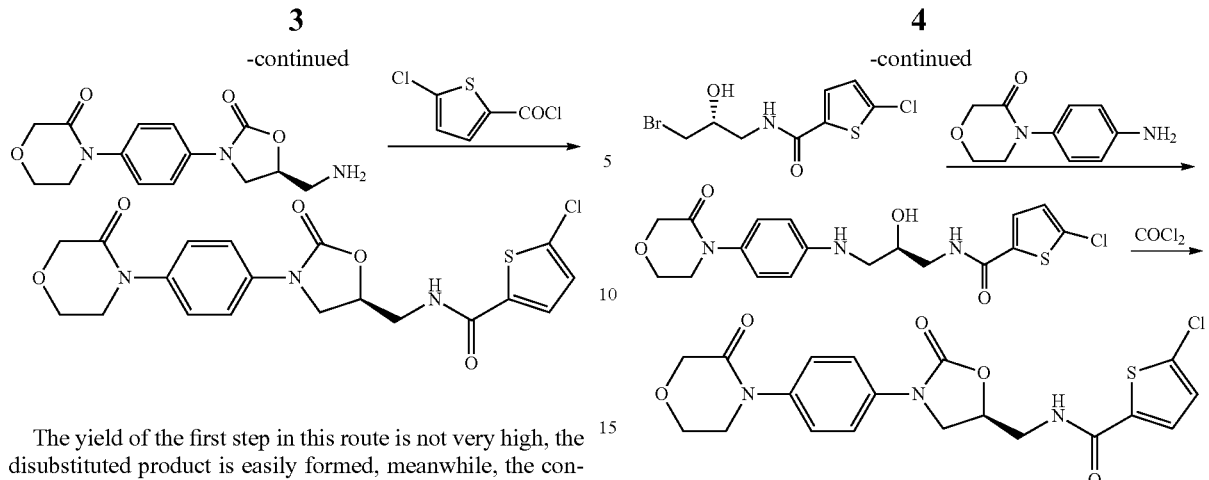

The yield of the first step in this route is not very high, the disubstituted product is easily formed, meanwhile, the configuration of the product of the first step is prone to be inversed and the formed isomer is difficult to separate, which will get into the following reactions until the final product Rivaroxaban, and influence its quality.

3, U.S. Pat. No. 7,816,355 disclosed the following synthesis route:

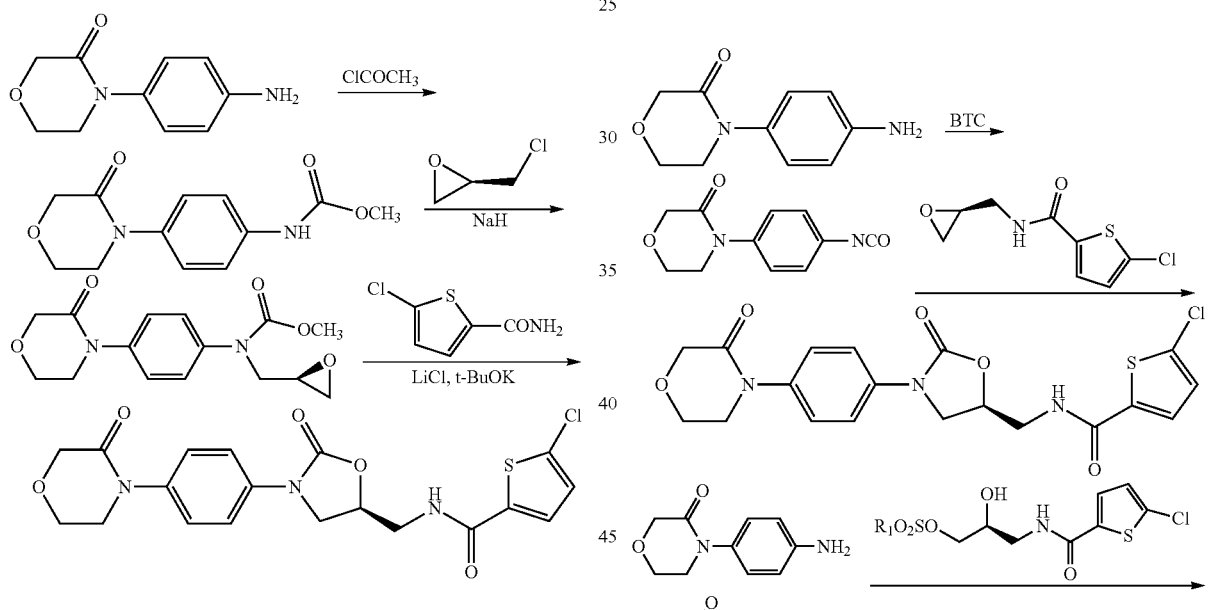

This route is short, but dangerous reagents are used during the process, such as methyl chloroformate and sodium hydride etc., and the yield of cyclization is low, which is not suitable for production in an industrial scale.

4, WO2005068456 and DE10300111 disclosed the following synthesis route:

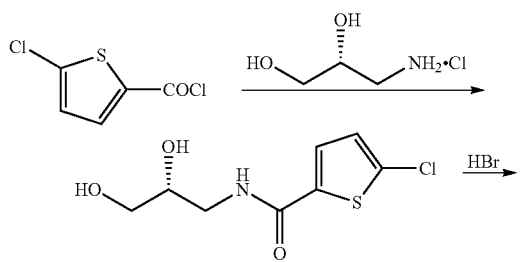

3-Aminopropane-1,2-diol, the raw material for the first step of the route, is expensive and hypertoxic phosgene is used in the process of cyclization, which is not suitable for production in an industrial scale.

5, WO2011098501 disclosed two following synthesis routes:

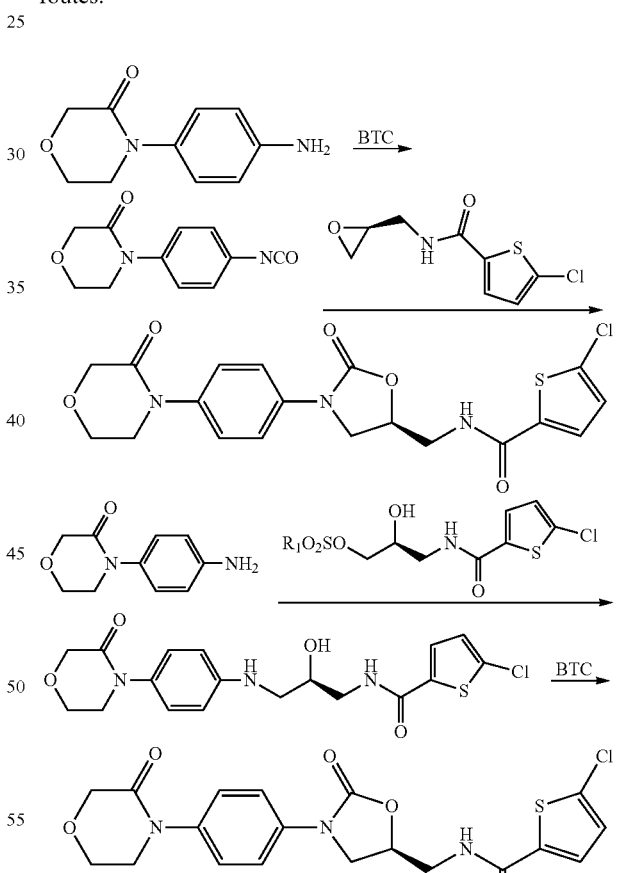

In the first route, Rivaroxaban is prepared by isocyanate and (S)-5-chloro-N-(oxiran-2-ylmethyl)thiophene-2-carboxamide via cyclization directly, but (S)-5-chloro-N-(oxiran-2-ylmethyl)thiophene-2-carboxamide is expensive and the yield is low, which is only 55%. The yield of the step of cyclization with triphosgene in the second route is much lower, which is only 21.1%.

Content of the Present Invention

The technical problem to be solved in the present invention is for overcoming tough preparation condition, low yield, difficult byproduct separation, high cost, complicated process and disadvantages in production in an industrial scale to provide a method for preparing Rivaroxaban intermediate. The method provided in the present invention has mild preparation condition, simple process, low cost, high yield, easy purification process for the product, which is suitable for production in an industrial scale.

The present invention provides a method for preparing Rivaroxaban intermediate I, comprising: in a non-protonic solvent, under the effect of lewis acid, performing cyclization reaction with 4-(4-isocyanatophenyl)morpholin-3-one (II) and (S)-epoxy compound (III), reaction temperature ranging from 20° C. to 160° C.;

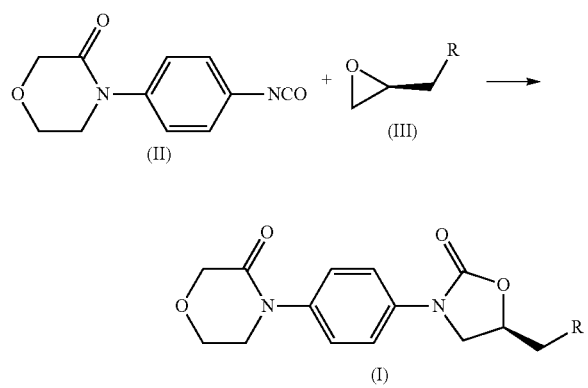

wherein R is an amino substituted by an amino protecting group.

The non-protonic solvent is selected from the group consisting of esters, ketones, $C_6$~$C_{10}$ alkanes, halohydrocarbons, ethers, substituted benzene, dioxane, tetrahydrofuran, N,N-dimethylamide, nitriles and sulfoxides, preferably ethyl acetate, butyl acetate, isoamyl acetate, toluene, xylene, chlorobenzene, o-dichlorobenzene, tetrahydrofuran, dichoromethane, N,N-dimethylformamide, $C_{6-8}$ straight-chain or branched-chain alkanes, acetone, 1,4-dioxane and acetonitrile, more preferably ethyl acetate, isoamyl acetate, butyl acetate, xylene, N,N-dimethylformamide and tetrahydrofuran. Preferably, an amount of the non-protonic solvent is 10~30 mL per gram of compound II, more preferably, 15~25 mL per gram of compound II and most preferably, 18~20 mL per gram of compound II.

The lewis acid is preferably selected from the group consisting of lithium bromide, magnesium bromide, lithium chloride, magnesium chloride, magnesium iodide, lithium iodide, lithium chloride, zinc chloride, tetra-n-butylammonium bromide and tetra-n-butylammonium chloride, more preferably, lithium bromide, magnesium bromide, n-butylammonium bromide and magnesium iodide. The molar ratio of the lewis acid to compound II is preferably 0.02~0.18, more preferably 0.07~0.13, and most preferably 0.09~0.11.

The amino protecting group is acceptable in the art. The amino substituted by an amino protecting group is preferably selected from one of the following group:

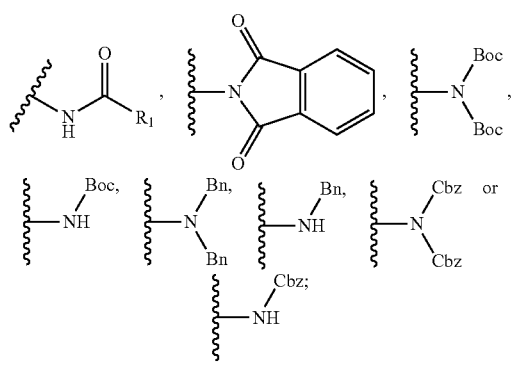

wherein, $R_1$ is hydrogen or a $C_{1-6}$ straight-chain or branched-chain alkyl, Boc is a tert-butoxycarbonyl group, Bn is a benzyl group and Cbz is a benzyloxycarbonyl group.

More preferably, the amino substituted by an amino protecting group is phthalimido, having the structure:

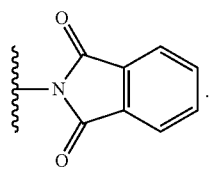 [SMILES: *N1C(=O)c2ccccc2C1=O]

The molar ratio of the (S)-epoxy compound (III) to 4-(4-isocyanatophenyl)morpholin-3-one (II) is preferably 0.8~1.3, more preferably 1.05~1.15, and most preferably 1.1.

The reaction temperature preferably ranges from 100° C. to 140° C., and more preferably from 115° C. to 125° C.

The process of the cyclization reaction can be monitored by TLC or HPLC. Generally, the reaction is regarded as finishing when compound II disappears.

After the cyclization reaction, post-processing can be performed to obtain pure Rivaroxaban intermediate. The post-processing preferably comprises: filtrating the reaction system. Preferably, the filtration is suction filtration.

The Rivaroxaban intermediate I is an important intermediate in preparing Rivaroxaban, which can prepare Rivaroxaban though reacting with 5-chlorothiophene-2-formyl chloride after removing the amino protecting group. The reaction formula is illustrated as:

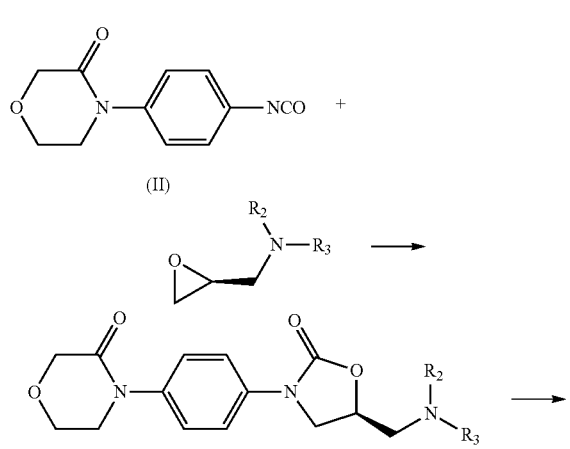

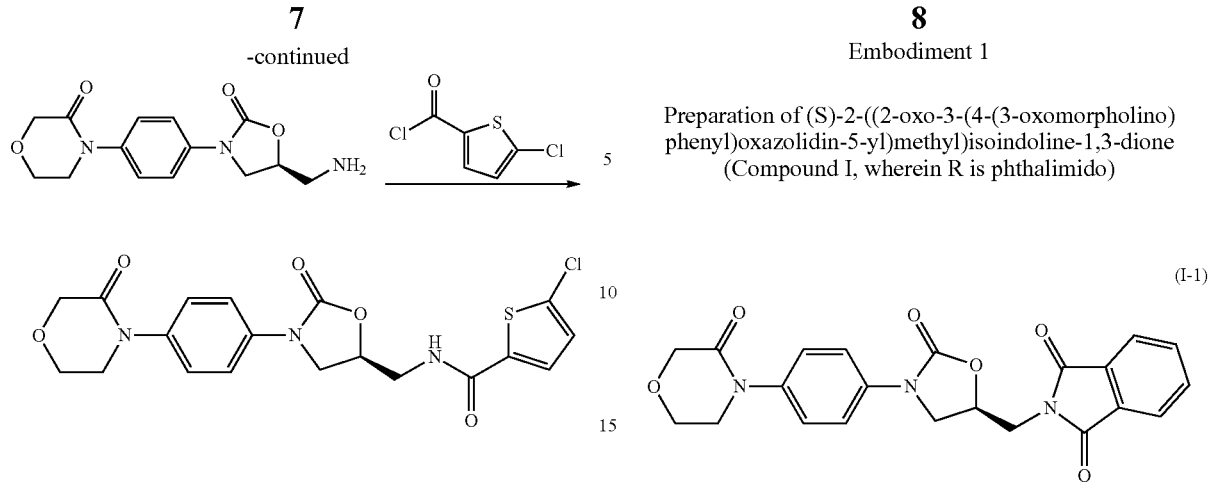

In the present invention, the preferred conditions of the preparation method can be any combination, i.e. preferred examples of the present invention is obtained.

Compound (II) can be prepared according to the method disclosed in WO2011098501.

Compound (III) can be prepared according to the method disclosed in EP1403267.

The raw materials used in the present invention can be commercial available.

The positive effects of the present invention rely in that the method in the present invention has several advantages, such as simple process, mild preparation condition, high total yield, high purity of the product, and compared to other routes described elsewhere, no dangerous reagent is used, such as butyllithium and sodium azide. Furthermore, no tough conditions are required like low-temperature. Therefore, the method provided in the present invention is suitable for production in an industrial scale.

DETAILED DESCRIPTION OF THE PREFERRED EMBODIMENT

The following examples further illustrate the present invention, but the present invention is not limited thereto. The experiments without giving the specific reaction conditions could be performed under the guidance of conventional approach or product datasheet.

Reference Embodiment 1

Preparation of 4-(4-isocyanatophenyl)morpholin-3-one (II)

A solution of 4-(4-anilino)morpholin-3-one in isoamyl acetate (3.64 g, 100 mL) was added dropwise in a solution of triphosgene in isoamyl acetate (3.49 g, 10 mL), refluxed for 2 h, and white solid (3.77 g, 91.3%) was obtained by rotary evaporation under reduced pressure.

ESI-MS (m/z): 219 (M+H); IR (cm$^{-1}$), 2270 (N=C=O);

$^1$HNMR (400 MHz, CDCl$_3$) δ: 3.75 (m, 2H), 4.02 (m, 2H), 4.30 (s, 2H), 7.13 (d, 1H), 7.32 (d, 1H), 7.40 (d, 1H), 7.58 (d, 1H).

Embodiment 1

Preparation of (S)-2-((2-oxo-3-(4-(3-oxomorpholino)phenyl)oxazolidin-5-yl)methyl)isoindoline-1,3-dione (Compound I, wherein R is phthalimido)

(S)-2-(oxiran-2-ylmethyl)isoindoline-1,3-dione (3.87 g, 19.06 mmol, 1.1 eq.) and 4-(4-isocyanatophenyl)morpholin-3-one (3.77 g, 17.29 mmol) were dissolved in ethyl acetate (70 mL) respectively, lithium bromide (0.15 g, 1.74 mmol) was added at 20° C., reacted for 12 h. White solid was obtained by filtration (6.11 g, yield: 83.86%).

ESI-MS (m/z): 422 (M+H), 444 (M+Na);

$^1$HNMR (400 MHz, CDCl$_3$) δ: 3.74 (m, 2H), 3.94 (m, 4H), 4.10 (m, 2H), 4.32 (s, 2H), 4.98 (m, 1H), 7.34 (d, 2H), 7.56 (d, 2H), 7.75 (m, 2H), 7.88 (m, 2H);

HPLC: 99.10%.

Embodiment 2

Preparation of (S)-2-((2-oxo-3-(4-(3-oxomorpholino)phenyl)oxazolidin-5-yl)methyl)isoindoline-1,3-dione (Compound I, wherein R is phthalimido)

(S)-2-(oxiran-2-ylmethyl)isoindoline-1,3-dione (3.51 g, 17.29 mmol, 1.0 eq.) and 4-(4-isocyanatophenyl)morpholin-3-one (3.77 g, 17.29 mmol) were dissolved in toluene (70 mL) respectively and heated to 100° C. Then lithium bromide (0.15 g, 1.74 mmol) was added, and the mixture was reacted for 4 h. White solid was obtained by filtration (6.50 g, yield: 89.28%).

ESI-MS (m/z): 422 (M+H), 444 (M+Na);

$^1$HNMR (400 MHz, CDCl$_3$) δ: 3.74 (m, 2H), 3.94 (m, 4H), 4.10 (m, 2H), 4.32 (s, 2H), 4.98 (m, 1H), 7.34 (d, 2H), 7.56 (d, 2H), 7.75 (m, 2H), 7.88 (m, 2H).

HPLC: 99.10%.

Embodiment 3

Preparation of (S)-2-((2-oxo-3-(4-(3-oxomorpholino)phenyl)oxazolidin-5-yl)methyl)isoindoline-1,3-dione (Compound I, wherein R is phthalimido)

(S)-2-(oxiran-2-ylmethyl)isoindoline-1,3-dione (3.87 g, 19.06 mmol, 1.1 eq.) and 4-(4-isocyanatophenyl)morpholin-3-one (3.77 g, 17.29 mmol) were dissolved in chlorobenzene (70 mL) respectively, then heated to 115° C. and lithium iodide (0.23 g, 1.72 mmol) was added. The mixture was reacted for 4 h, white solid was obtained by filtration (6.85 g, yield: 94.09%).

ESI-MS (m/z): 422 (M+H), 444 (M+Na);

¹HNMR (400 MHz, CDCl₃) δ: 3.74 (m, 2H), 3.94 (m, 4H), 4.10 (m, 2H), 4.32 (s, 2H), 4.98 (m, 1H), 7.34 (d, 2H), 7.56 (d, 2H), 7.75 (m, 2H), 7.88 (m, 2H);
HPLC: 98.91%.

Embodiment 4

Preparation of (S)-2 ((2-oxo-3-(4-(3-oxomorpholino) phenyl)oxazolidin-5-yl)methyl)isoindoline-1,3-dione (Compound I, wherein R is phthalimido)

(S)-2-(oxiran-2-ylmethyl)isoindoline-1,3-dione (4.56 g, 22.46 mmol, 1.3 eq.) and 4-(4-isocyanatophenyl)morpholin-3-one (3.77 g, 17.29 mmol) were dissolved in isoamyl acetate (70 mL) respectively, and heated to 120° C. Then magnesium chloride (0.12 g, 1.28 mmol) was added, the mixture was reacted for 4 h, white solid was obtained by filtration (6.97 g, yield: 95.5%).
ESI-MS (m/z): 422 (M+H), 444 (M+Na);
¹HNMR (400 MHz, CDCl₃) δ: 3.74 (m, 2H), 3.94 (m, 4H), 4.10 (m, 2H), 4.32 (s, 2H), 4.98 (m, 1H), 7.34 (d, 2H), 7.56 (d, 2H), 7.75 (m, 2H), 7.88 (m, 2H);
HPLC: 98.82%.

Embodiment 5

Preparation of (S)-2((2-oxo-3-(4-(3-oxomorpholino) phenyl)oxazolidin-5-yl)methyl)isoindoline-1,3-dione (Compound I, wherein R is phthalimido)

(S)-2-(oxiran-2-ylmethyl)isoindoline-1,3-dione (3.87 g, 19.06 mmol, 1.1 eq.) and 4-(4-isocyanatophenyl)morpholin-3-one (3.77 g, 17.29 mmol) were dissolved in xylenen (70 mL) respectively and heated to 125° C. Then lithium bromide (0.15 g, 1.74 mmol) was added, the mixture was reacted for 4 h, white solid was obtained by filtration (6.89 g, yield: 94.64%).
ESI-MS (m/z): 422 (M+H), 444 (M+Na);
¹HNMR (400 MHz, CDCl₃) δ: 3.74 (m, 2H), 3.94 (m, 4H), 4.10 (m, 2H), 4.32 (s, 2H), 4.98 (m, 1H), 7.34 (d, 2H), 7.56 (d, 2H), 7.75 (m, 2H), 7.88 (m, 2H);
HPLC: 99.04%.

Embodiment 6

Preparation of (S)-2-((2-oxo-3-(4-(3-oxomorpholino) phenyl)oxazolidin-5-yl)methyl)isoindoline-1,3-dione (Compound I, wherein R is phthalimido)

(S)-2-(oxiran-2-ylmethyl)isoindoline-1,3-dione (3.87 g, 19.06 mmol, 1.1 eq.) and 4-(4-isocyanatophenyl)morpholin-3-one (3.77 g, 17.29 mmol) were dissolved in N,N-dimethylformamide (70 mL) respectively and heated to 140° C. Then lithium bromide (0.15 g, 1.74 mmol) was added, the mixture was reacted for 4 h, white solid was obtained by filtration (6.68 g, yield: 91.75%).
ESI-MS (m/z): 422 (M+H), 444 (M+Na);
¹HNMR (400 MHz, CDCl₃) δ: 3.74 (m, 2H), 3.94 (m, 4H), 4.10 (m, 2H), 4.32 (s, 2H), 4.98 (m, 1H), 7.34 (d, 2H), 7.56 (d, 2H), 7.75 (m, 2H), 7.88 (m, 2H);
HPLC: 98.70%.

Embodiment 7

Preparation of (S)-2-((2-oxo-3-(4-(3-oxomorpholino) phenyl)oxazolidin-5-yl)methyl)isoindoline-1,3-dione (Compound I, wherein R is phthalimido)

(S)-2-(oxiran-2-ylmethyl)isoindoline-1,3-dione (3.87 g, 19.06 mmol, 1.1 eq.) and 4-(4-isocyanatophenyl)morpholin-3-one (3.77 g, 17.29 mmol) were dissolved in o-dichlorobenzene (70 mL) respectively and heated to 160° C. Then lithium bromide (0.15 g, 1.74 mmol) was added, the mixture was reacted for 4 h, white solid was obtained by filtration (6.46 g, yield: 88.66%).
ESI-MS (m/z): 422 (M+H), 444 (M+Na);
¹HNMR (400 MHz, CDCl₃) δ: 3.74 (m, 2H), 3.94 (m, 4H), 4.10 (m, 2H), 4.32 (s, 2H), 4.98 (m, 1H), 7.34 (d, 2H), 7.56 (d, 2H), 7.75 (m, 2H), 7.88 (m, 2H);
HPLC: 98.29%.

Embodiment 8

Preparation of (S)-2-((2-oxo-3-(4-(3-oxomorpholino) phenyl)oxazolidin-5-yl)methyl)isoindoline-1,3-dione (Compound I, wherein R is phthalimido)

(S)-2-(oxiran-2-ylmethyl)isoindoline-1,3-dione (3.69 g, 18.14 mmol, 1.05 eq.) and 4-(4-isocyanatophenyl)morpholin-3-one (3.77 g, 17.29 mmol) were dissolved in butyl acetate (70 mL) respectively, heated to 120° C. Then a solution of magnesium iodide in diethyl ether (0.3 mmol, 0.3 mL) was added, the mixture was reacted for 4 h, white solid was obtained by filtration (6.88 g yield: 94.50%).
ESI-MS (m/z): 422 (M+H), 444 (M+Na);
¹HNMR (400 MHz, CDCl₃) δ: 3.74 (m, 2H), 3.94 (m, 4H), 4.10 (m, 2H), 4.32 (s, 2H), 4.98 (m, 1H), 7.34 (d, 2H), 7.56 (d, 2H), 7.75 (m, 2H), 7.88 (m, 2H).
HPLC: 98.85%.

Embodiment 9

Preparation of (S)-2-((2-oxo-3-(4-(3-oxomorpholino) phenyl)oxazolidin-5-yl)methyl)isoindoline-1,3-dione (Compound I, wherein R is phthalimido)

(S)-2-(oxiran-2-ylmethyl)isoindoline-1,3-dione (3.87 g, 19.06 mmol, 1.1 eq.) and 4-(4-isocyanatophenyl)morpholin-3-one (3.77 g, 17.29 mmol) were dissolved in tetrahydrofuran (70 mL) respectively and then heated to reflux. Then lithium bromide (0.15 g, 1.74 mmol) was added, the mixture was reacted for 4 h, white solid was obtained by filtration (6.45 g, yield: 88.4%).
ESI-MS (m/z): 422 (M+H), 444 (M+Na);
¹HNMR (400 MHz, CDCl₃) δ: 3.74 (m, 2H), 3.94 (m, 4H), 4.10 (m, 2H), 4.32 (s, 2H), 4.98 (m, 1H), 7.34 (d, 2H), 7.56 (d, 2H), 7.75 (m, 2H), 7.88 (m, 2H);
HPLC: 99.11%.

Embodiment 10

Preparation of (S)-2-((2-oxo-3-(4-(3-oxomorpholino) phenyl)oxazolidin-5-yl)methyl)isoindoline-1,3-dione (Compound I, wherein R is phthalimido)

(S)-2-(oxiran-2-ylmethyl)isoindoline-1,3-dione (3.87 g, 19.06 mmol, 1.1 eq.) and 4-(4-isocyanatophenyl)morpholin-3-one (3.77 g, 17.29 mmol) were dissolved in n-heptane (70 mL) respectively, and heated to reflux. Lithium bromide (0.15 g, 1.74 mmol) was added, the mixture was reacted for 4 h, white solid was obtained by filtration (6.53 g, yield: 89.5%).
ESI-MS (m/z): 422 (M+H), 444 (M+Na);
¹HNMR (400 MHz, CDCl₃) δ: 3.74 (m, 2H), 3.94 (m, 4H), 4.10 (m, 2H), 4.32 (s, 2H), 4.98 (m, 1H), 7.34 (d, 2H), 7.56 (d, 2H), 7.75 (m, 2H), 7.88 (m, 2H).
HPLC: 98.95%.

Embodiment 11

Preparation of (S)-2-((2-oxo-3-(4-(3-oxomorpholino) phenyl)oxazolidin-5-yl)methyl)isoindoline-1,3-dione (Compound I, wherein R is phthalimido)

(S)-2-(oxiran-2-ylmethyl)isoindoline-1,3-dione (4.04 g, 19.87 mmol, 1.15 eq.) and 4-(4-isocyanatophenyl)morpholin-3-one (3.77 g, 17.29 mmol) were dissolved in 1,4-dioxane (70 mL) respectively, then heated to 120° C. and magnesium bromide (0.22 g, 1.21 mmol) was added. The mixture was reacted for 4 h, white solid was obtained by filtration (6.94 g, yield: 95.1%).
ESI-MS (m/z): 422 (M+H), 444 (M+Na);
$^1$HNMR (400 MHz, CDCl$_3$) δ: 3.74 (m, 2H), 3.94 (m, 4H), 4.10 (m, 2H), 4.32 (s, 2H), 4.98 (m, 1H), 7.34 (d, 2H), 7.56 (d, 2H), 7.75 (m, 2H), 7.88 (m, 2H);
HPLC: 99.15%.

Embodiment 12

Preparation of (S)-2-((2-oxo-3-(4-(3-oxomorpholino) phenyl)oxazolidin-5-yl)methyl)isoindoline-1,3-dione (Compound I, wherein R is phthalimido)

(S)-2-(oxiran-2-ylmethy)isoindoline-1,3-dione (3.87 g, 19.06 mmol, 1.1 eq.) and 4-(4-isocyanatophenyl)morpholin-3-one (3.77 g, 17.29 mmol) were dissolved in acetonitrile (70 mL) respectively, then heated to reflux. Tetra-n-butylammonium bromide (0.55 g, 1.71 mmol) was added, the mixture was reacted for 4 h, white solid was obtained by filtration (6.57 g, yield: 90.0%).
ESI-MS (m/z): 422 (M+H), 444 (M+Na);
$^1$HNMR (400 MHz, CDCl$_3$) δ: 3.74 (m, 2H), 3.94 (m, 4H), 4.10 (m, 2H), 4.32 (s, 2H), 4.98 (m, 1H), 7.34 (d, 2H), 7.56 (d, 2H), 7.75 (m, 2H), 7.88 (m, 2H);
HPLC: 98.86%.

Embodiment 13

Preparation of (S)—N-((2-oxo-3-(4-(3-oxomorpholino)phenyl)oxazolidin-5-yl)methyl)benzylamine (Compound I, wherein R is benzylamino)

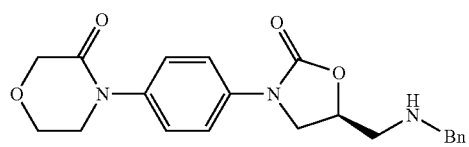

(I-2)

(S)—N-benzyl-1-(oxiran-2-ylmethyl)methylamine (3.10 g, 19.06 mmol, 1.1 eq.) and 4-(4-isocyanatophenyl)morpholin-3-one (3.77 g, 17.29 mmol) were dissolved in butanone (70 mL) respectively, and heated to reflux. Then lithium bromide (0.15 g, 1.74 mmol) was added, the mixture was reacted for 4 h, white solid was obtained by filtration (5.88 g, yield: 89.21%).
ESI-MS (m/z): 382 (M+1), 404 (M+Na);
$^1$HNMR (400 MHz, CDCl$_3$) δ: 2.0 (s, 1H), 2.82 (d, 2H), 122 (t, 2H), 3.50 (t, 2H), 3.55 (t, 2H), 3.82 (s, 2H), 4.31 (s, 2H), 4.86 (s, 1H), 6.76 (d, 2H), 7.35 (d, 2H), 7.23-7.26 (m, 3H), 7.36 (dd, 2H).
HPLC: 99.02%.

Embodiment 14

Preparation of (S)—N-((2-oxo-3-(4-(3-oxomorpholino)phenyl)oxazolidin-5-yl)methyl)dibenzylamine (Compound I, wherein R is dibenzylamino)

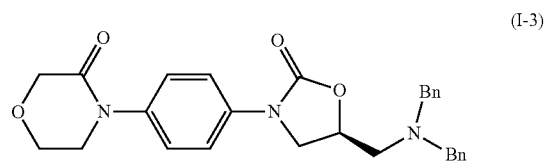

(I-3)

White solid having the structure as I-3 (7.72 g, yield: 94.76%) was prepared according to the embodiment 3, except for that (S)-2-(oxiran-2-ylmethyl)isoindoline-1,3-dione (3.87 g, 19.06 mmol) was replace by (S)—N,N-dibenzyl-1-(oxiran-2-ylmethyl)methylamine (4.81 g, 19.06 mmol, 1.1 eq.).
ESI-MS (m/z): 472 (M+H), 494 (M+Na);
$^1$HNMR (400 MHz, CDCl$_3$) δ: 2.61 (m, 2H), 3.20 (t, 2H), 3.52 (t, 2H), 3.56 (t, 2H), 3.62 (s, 4H), 4.31 (s, 2H), 4.92 (s, 1H), 7.23 (dd, 4H), 7.26 (m, 2H), 7.32 (dd, 4H), 7.36 (d, 2H), 7.56 (d, 2H);
HPLC: 99.13%.

Embodiment 15

Preparation of (S)-(tert-butyl) ((2-oxo-3-(4-(3-oxomorpholino)phenyl)oxazolidin-5-yl)methyl)carbamate (Compound I, wherein R is tert-butoxycarbonyl amino)

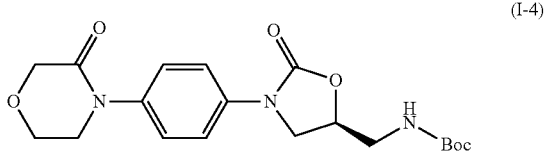

(I-4)

White solid having the structure as I-4 (6.21 g, yield: 91.83%) was prepared according to the embodiment 3, except for that (S)-2-(oxiran-2-ylmethyl)isoindoline-1,3-dione (3.87 g, 19.06 mmol) was replaced by (S)-(tert-butyl) oxiran-2-ylmethyl-carbamate (3.29 g, 19.06 mmol, 1.1 eq.).
ESI-MS (m/z): 392 (M+1), 414 (M+Na);
$^1$HNMR (400 MHz, CDCl$_3$) δ: 1.38 (s, 9H), 3.10 (d, 2H), 3.38 (d, 2H), 3.52-3.55 (m, 4H), 4.30 (s, 2H), 5.15 (dd, 1H), 6.84 (d, 2H), 7.34 (d, 2H), 8.04 (s, 1H);
HPLC: 98.87%.

Embodiment 16

Preparation of (S)-benzyl((2-oxo-3-(4-(3-oxomorpholino)phenyl)oxazolidin-5-yl)methyl)carbamate (Compound I, wherein R is benzyloxycarbonyl amino)

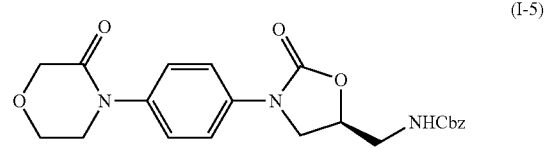 [SMILES: O=C(NC[C@H]1CN(c2ccc(N3CCOCC3=O)cc2)C(=O)O1)OCc1ccccc1]

(I-5)

White solid having the structure as 1-5 (6.79 g, yield: 92.38%) was prepared according to the embodiment 3, except for that (S)-2-(oxiran-2-ylmethyl)isoindoline-1,3-dione (3.87 g, 19.06 mmol) was replaced by (S)-benzyl oxiran-2-ylmethyl-carbamate (3.94 g, 19.06 mmol, 1.1 eq.).

ESI-MS (m/z): 426 (M+1), 448 (M+Na);

$^1$HNMR (400 MHz, CDCl$_3$) δ: 3.30 (d, 2H), 3.38 (d, 2H), 3.52-3.55 (m, dH), 4.31 (s, 2H), 5.10 (s, 2H), 5.21 (dd, 1H), 6.36 (d, 2H), 6.75 (d, 2H), 7.38-7.47 (m, 6H), 8.02 (s, 1H);

HPLC: 98.76%.

Comparative embodiment 1

Preparation of Rivaroxaban

White solid was obtained (3.23 g, yield: 42.89%) according to the embodiment 3, except for that (S)-5-chloro-N-(oxiran-2-ylmethyl)thiophene-2-formamide (4.14 g, 19.06 mmol, 1.1 eq.) was used to replace (S)-2-(oxiran-2-ylmethyl)isoindoline-1,3-dione (3.87 g, 19.06 mmol), wherein 5-chlorothiophene-2-formyl is not an conventional amino protecting group in the art.

HPLC: 98.65%.

What is claimed is:

1. A method for preparing Rivaroxaban intermediate I, comprising: in a non-protonic solvent, under the effect of a lewis acid, performing cyclization reaction with compound II and compound III, reaction temperature ranging from 20° C. to 160° C.,

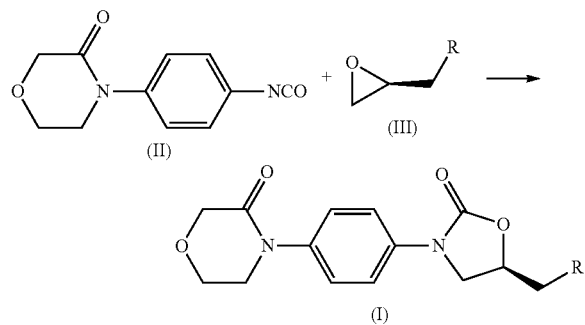

wherein R is an amino substituted by an amino protecting group.

2. The method according to claim 1, wherein the non-protonic solvent is selected from the group consisting of ether acetate, butyl acetate, isoamyl acetate, toluene, chlorobenzene, xylene, o-dichlorobenzene, tetrahydrofuran, N,N-dimethylformamide, $C_{6-8}$ straight-chain or branched-chain alkanes, butanone, 1,4-dioxane and acetonitrile.

3. The method according to claim 1, wherein the lewis acid is selected from the group consisting of lithium bromide, magnesium bromide, lithium chloride, magnesium chloride, magnesium iodide, lithium iodide, lithium chloride, zinc chloride, tetra-n-butylammonium bromide and tetra-n-butylammonium chloride.

4. The method according to claim 1, wherein the molar ratio of the lewis acid to the compound II is 0.02-0.18.

5. The method according to claim 4, wherein the molar ratio of the lewis acid to the compound II is 0.07-0.13.

6. The method according to claim 5, wherein the molar ratio of the lewis acid to the compound II is 0.09-0.11.

7. The method according to claim 1, wherein the structure of R is represented by a formula selected from the group consisting of:

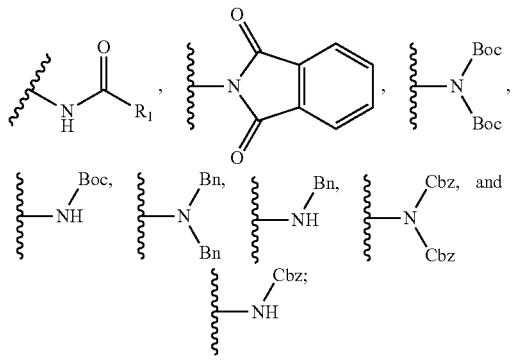

Wherein $R_1$ is hydrogen or a $C_{1-6}$ straight-chain or branched-chain alkyl, Boc is a tert-butoxycarbonyl group, Bn is a benzyl group and Cbz is a benzyloxycarbonyl group.

8. The method according to claim 1, wherein the molar ratio of the compound III to the compound II is 0.8-1.3.

9. The method according to claim 8, wherein the molar ratio of the compound III to the compound II is 1.05-1.15.

10. The method according to claim 1, wherein the reaction temperature ranges from 100° C. to 140° C.

11. The method according to claim 10, wherein the reaction temperature ranges from 115° C. to 125° C.

* * * * *